(12) United States Patent
Hachenberg et al.

(10) Patent No.: US 9,393,088 B2
(45) Date of Patent: Jul. 19, 2016

(54) METHOD FOR THE MANUFACTURE OF A SHAPED BODY AS WELL AS A GREEN COMPACT

(75) Inventors: Jörg Hachenberg, Aschaffenburg (DE); Rudi Steinke, Hanau (DE); Markus Vollmann, Gelnhausen (DE); Irmgard Wissel, Freigericht (DE); Gerhard Zellmann, Linsengericht (DE); Elmar Hock, Mombris (DE); Stefan Fecher, Johannesberg (DE); Lothar Volkl, Goldbach (DE)

(73) Assignee: DEGUDENT GMBH, Hanau (DE)

( * ) Notice: Subject to any disclaimer, the term of this patent is extended or adjusted under 35 U.S.C. 154(b) by 1264 days.

(21) Appl. No.: 13/292,132

(22) Filed: Nov. 9, 2011

(65) Prior Publication Data

US 2012/0114516 A1     May 10, 2012

(30) Foreign Application Priority Data

Nov. 9, 2010 (EP) .................................. 10190512

(51) Int. Cl.
| | |
|---|---|
| A61C 13/00 | (2006.01) |
| B22F 7/00 | (2006.01) |
| B22F 3/11 | (2006.01) |
| A61K 6/04 | (2006.01) |
| B22F 3/10 | (2006.01) |
| B22F 3/24 | (2006.01) |
| C22C 19/05 | (2006.01) |
| C22C 19/07 | (2006.01) |

(52) U.S. Cl.
CPC ............... *A61C 13/0022* (2013.01); *A61K 6/04* (2013.01); *B22F 3/1021* (2013.01); *B22F 3/24* (2013.01); *C22C 19/05* (2013.01); *C22C 19/053* (2013.01); *C22C 19/07* (2013.01)

(58) Field of Classification Search
CPC ............ A61C 13/0022; B22F 2203/11; B22F 2998/00; B22F 2998/10; B22F 2999/00
See application file for complete search history.

(56) References Cited

U.S. PATENT DOCUMENTS

| | | | |
|---|---|---|---|
| 4,996,022 A | | 2/1991 | Shindo et al. |
| 7,658,781 B1 * | | 2/2010 | Waggoner et al. .............. 75/236 |
| 2005/0023710 A1 | | 2/2005 | Brodkin et al. |
| 2005/0023717 A1 | | 2/2005 | Watanuki |
| 2010/0154587 A1 * | | 6/2010 | Eason .............................. 75/230 |

FOREIGN PATENT DOCUMENTS

| | | |
|---|---|---|
| CN | 101139664 A | 3/2008 |
| CN | 101240382 A | 8/2008 |
| CN | 101646402 A | 2/2010 |
| DE | 103 42 231 | 5/2005 |
| EP | 1 764 062 | 3/2007 |
| WO | WO 99/47065 | 9/1999 |
| WO | WO 01/12097 | 2/2001 |
| WO | WO 2009/030291 | 3/2009 |
| WO | WO 2009/120749 | 10/2009 |

OTHER PUBLICATIONS

J.J. Dunkley, "Atomization," Metal Powder Production and Characterization, vol. 7, Powder Metal Technologies and Applications, ASM Handbook, ASM International, 1998, pp. 35-52 (print), 3 pages total (online).*

Chinese Office Action issued Oct. 28, 2014, corresponding to Chinese Patent Application 201110420936.6.

Rodrigues, W.C., et al., "Powder metallurgical processing of Co-28%Cr-6%Mo for dental implants: Physical, mechanical and electrochemical properties", Powder Technology, Bd. 206. Nr. 3. Sep. 29, 2010. XP-002632108.

\* cited by examiner

*Primary Examiner* — Scott Kastler
*Assistant Examiner* — Vanessa Luk
(74) *Attorney, Agent, or Firm* — Ladas & Parry LLP

(57) ABSTRACT

A method for manufacturing a shaped body, comprising creating a mixture of a metal powder and binding agent, compacting the mixture to form a green compact, heating the green compact to a debinding start temperature $T_1$, debinding the green compact by controlled heating of the green compact from start temperature $T_1$ to end temperature $T_2$ at a heat-up rate $R_1$, presintering the debindered green compact to the presinter end temperature $T_{VS}$ at a heat-up rate $R_{HVS}$, cooling the green compact from the presinter end temperature $T_{VS}$ at a cool-down rate $R_{KVS}$, whereby at least the heat-up rate $R_{HVS}$, the presinter end temperature $T_{VS}$, and the cool-down rate $R_{KVS}$ are tuned relative to each other in such a way that the presintered green compact forming a blank has a surface porosity of 16% to 22% after presintering, and machining and sintering of the blank to form the shaped body.

41 Claims, No Drawings

METHOD FOR THE MANUFACTURE OF A SHAPED BODY AS WELL AS A GREEN COMPACT

The invention relates to a method for the manufacture of a shaped body, in particular of a dental prosthesis or part thereof, by way of mixing of a metal powder.

The invention also relates to a green compact for the manufacture of a dental prosthesis or of a part thereof.

In recent times CAD/CAM technology (Computer Aided Design, Computer Aided Manufacturing) is more frequently being used in the manufacture of dental prostheses such as crowns or bridges, whereby CAD/CAM is applied in particular in the area of ceramics. EP-B-1 067 880 should be referenced as an example for this.

DE-C-199 38 144 describes a method for the manufacture of dental prostheses, whereby a ceramic-based presintered moulded blank is machined using a milling process and subsequently is sintered to full density.

WO-2009/120749 discloses the use of a CAD/CAM milling process in the manufacture of a dental prosthesis. For this purpose, at first a metal powder is mixed with a binding agent, whereupon a moulded blank is produced by way of metal powder injection moulding. A milling process is used to create a shaped body from this, which corresponds to the dental prosthesis to be produced taking into account the contraction occurring during sintering.

In accordance with EP-A-1 764 062, a shaped body produced from a dental alloy consists of a dental alloy powder that is sintered to full density by hot-isostatic pressing.

In accordance with DE-A-103 42 231 it is known to manufacture a shaped body using powder-metallurgical processes, whereby during the machining the body is open-pored and has not been sintered to full density. Only after the final shape has been created, the open pores of the shaped body are filled with a second alloy in a further processing step by means of an infiltration process. The use of two alloys is a disadvantage.

US-A-2005/0023717 discloses a method for the manufacture of dental restorations using a free-forming process, in particular a rapid-prototyping process. Favoured materials to be used are powders of non-oxidizing metals. Preferred use is given to noble metals.

The reference Rodrigues et al.: "Powder metallurgical Processing of Co-28% Cr-6% Mo for dental implants: Physical, cheanical and electrochemical properties" Powder Technology, 2006 (2011), 233-238, describes a method for the manufacture of restoration elements. In this, a biocompatible cobalt-chromium-molybdenum alloy is mixed with a moulding agent, is heated to a temperature suitable for burning out the moulding agent, and is subsequently sintered to full density.

U.S. Pat. No. 4,996,022 discloses a method for the manufacture of a sintered body. As starting material one uses a powdered metal such as iron or nickel.

An iron-powder mixture that contains up to 1% organic binding agent is used in the manufacture of a sintered moulded part in accordance with AT-A-505 698. A final sintering is performed after presintering and cooling.

The objective of the present invention is to further develop a method and a presintered green body of the above-mentioned type so as to provide a shaped body, in particular a dental prosthesis or part thereof, that can be manufactured with very low tolerances and allows problem-free wet or dry machining, whereby in particular it should be possible to use a ceramic material for veneering purposes. Disadvantages known in the art should be avoided.

Another objective is to provide a green compact that can be machined with high accuracy in a simple manner, in order to subsequently be able to use it to manufacture a highly precise shaped part, in particular a dental prosthesis or a part thereof.

In accordance with the invention, this objective is met chiefly though a method for the manufacture of a shaped body, in particular a dental prosthesis or a part thereof, that is characterized by the following process steps:

Producing a mixture of a metal powder and a binding agent,

Compacting the mixture to form a green compact,

Heating the green compact from room temperature to a debinding start temperature $T_1$, Debinding the green compact by controlled heating of the green compact from the debinding start temperature $T_1$ to a debinding end temperature $T_2$ at a heat-up rate $R_1$ in a manner that rules out damage to the green compact, Presintering the debindered green compact, whereby the green compact is heated to a presinter end temperature $T_{VS}$ at a heat-up rate $R_{HVS}$, Cooling the green compact from the presinter end temperature $T_{VS}$ at a cool-down rate $R_{KVS}$, whereby at least the heat-up rate $R_{HVS}$, the presinter end temperature $T_{VS}$, and the cool-down rate $R_{KVS}$ are tuned relative to each other in such a way that the presintered green compact forming a blank possesses a surface porosity between 16% and 22% after presintering, Material-removing machining of the blank, and Sintering the machined blank to final density to form the shaped body.

Surface porosity here denotes the fraction of the surface that is not filled with material if viewed in a metallographic section.

In particular it is intended to use as metal powder a dental metal alloy in form of a cobalt-chromium or nickel-chromium alloy.

For a cobalt-chromium alloy the composition should be chosen as follows:
Cobalt: 50% to 70% by weight
Chromium: 20% to 35% by weight
Molybdenum: 0% to 10% by weight
Tungsten: 0% to 20% by weight
Other elements: less than 10% by weight,
whereby the sum total is 100% by weight.

Also an option is the use of a nickel-chromium alloy of the following composition:
Nickel: 50% to 70% by weight
Chromium: 20% to 35% by weight
Molybdenum: 0% to 10% by weight
Tungsten: 0% to 20% by weight
Other elements: less than 10% by weight,
with a sum total of 100% by weight.

Other elements that may be considered are in particular manganese, silicon, and nickel in case of the cobalt-chromium alloy, cobalt in case of the nickel-chromium alloy, and beryllium, cadmium, lead, iron, aluminum, titanium, carbon, nitrogen, oxygen, sulphur and other elements with a weight fraction of less than 1%.

In particular it is intended that the mixture compacted into the green compact possess a surface porosity, corresponding to the volume porosity, of between 16% and 27%, preferably between 18% and 22%. This porosity is created by the areas of the green compact that are filled with air or binding agent in between the metal powder particles.

It is also intended that after heating of the green compact to the presinter end temperature $T_{VS}$, the green compact be held at the presinter end temperature $T_{VS}$ for the duration of a holding time $t_{VS}$ and subsequently be cooled at a cool-down rate $R_{KVS}$.

In particular it is suggested that the green compact be cooled at the cool-down rate $R_{KVS}$ to a temperature $T_3$, whereby in particular $T_3 \leq T_2$, 450° C.$\leq T_3 \leq$650° C., and preferably $T_3$ is approximately 600° C.

In this, debinding and presintering should be performed in the absence of oxygen, in particular under an inert gas atmosphere, particularly preferred under an argon atmosphere. Other options are a reducing atmosphere or vacuum.

For the debinding, the green compact preferably is heated to a debinding start temperature $T_1$ with 350° C.$\leq T_1 \leq$550° C. After reaching a temperature $T_1$, in particular reaching the temperature $T_1 \cong$450° C., a slow heating takes place, whereby the heat-up rate during the debinding process should not exceed 20 K/min. A preferred range for the heat-up rate is 1 K/min to 5 K/min. In particular it is intended that in the region above 500° C., in particular from above 550° C. to the debinding end temperature $T_2$, with 550° C.$\leq T_2 \leq$650° C., in particular $T_2 \cong$600° C., one choose a heat-up rate between 1 K/min and 5 K/min. After reaching the debinding end temperature $T_2$ the green compact should be held at this temperature for a duration $t_2$ with 1 min$\leq t_2 \leq$20 min. However, this is not obligatory and mainly dependent on the chosen heat-up rate.

Irrespective of the preferred parameters, which were provided as examples and shall not limit the scope of protection of the invention, the heating must be performed in such a manner that the debinding takes place in a controlled manner, so that the green compact is not damaged and rendered unserviceable. This controlled heating, which is essential to prevent damage to the green compact, can be performed by an average expert without any problems after carrying out several simple trials.

After debinding, heating to the presinter end temperature $T_{VS}$ takes place, whereby in principle the heating rate $R_{HVS}$ may be chosen freely.

In order to obtain the desired surface porosity of the presintered green compact of between 16% and 22%, in particular between 18% and 20%, the invention intends that the presinter end temperature $T_{VS}$, the heat-up rate $R_{HVS}$, possibly the holding time $t_{VS}$ at the presinter end temperature $T_{VS}$, and the cool-down rate $R_{KVS}$ be tuned relative to each other. In case of a very slow heating to the presinter end temperature $T_{VS}$, e.g. using a heat-up rate between 1 K/min and 10 K/min, it is not required that the debindered green compact be held at the presinter end temperature for a time period $t_{VS}$.

The cool-down rate may also be used to influence the holding time $t_{VS}$, in particular to the extreme degree that cool-down commences immediately upon reaching the presinter end temperature $T_{VS}$.

The relative tuning of the parameters for the purpose of obtaining the desired surface or volume porosity of between 16% and 22%, in particular between 18% and 20%, can be performed taking into account the details provided as examples in the following.

If for example the presinter end temperature $T_{VS}$ is in a range between 650° C. and 750° C., the heat-up rate $R_{HVS}$ and/or the cool-down rate $R_{KVS}$ should be between 1 K/min and 200 K/min, preferably between 1 K/min and 50 K/min, and particularly preferred between 1 K/min and 20 K/min, whereby after reaching the presinter end temperature $T_{VS}$, a holding time $t_{VS}$ of between 10 min and 200 min, in particular between 30 min and 100 min, particularly preferred between 50 min and 80 min, should be adhered to.

If the presinter end temperature $T_{VS}$ is between 750° C. and 850° C., the heat-up rate $R_{HVS}$ and/or the cool-down rate $R_{KVS}$ should be between 5 K/min and 200 K/min, in particular between 5 K/min and 20 K/min. After reaching the presinter end temperature $T_{VS}$, one should preferably choose a holding time $t_{VS}$ between 5 min and 60 min, in particular between 10 min and 30 min.

However, it is also possible to set the presinter end temperature $T_{VS}$ in the range between 850° C. and 950° C., for example. In this case, the heat-up rate $R_{HVS}$ and the cool-down rate $R_{KVS}$ should be in the range between 15 K/min and 200 K/min, preferably between 15 K/min and 50 K/min. Preferred holding times $t_{VS}$ at this presinter end temperature $T_{VS}$ are in the range between 5 min and 30 min, in particular between 10 min and 20 min.

In order to achieve the desired surface porosity or volume porosity of the presintered blank, the presinter end temperature may also be in the range between 950° C. and 1100° C. In this case, the heat-up rate $R_{HVS}$ and the cool-down rate $R_{KVS}$ should be between 30 K/min and 200 K/min, preferably between 30 K/min and 100 K/min. For the above parameters one preferably sets a holding time $t_{VS}$ 5 min$\leq t_{VS} \leq$20 min.

For a cobalt-chromium alloy of the above-described composition one preferably chooses a presinter end temperature between 650° C. and 750° C. and a holding time between 50 min and 70 min at the presinter end temperature $T_{VS}$, whereby the heat-up rates are in the range between 10 K/min and 30 K/min.

In other words: various heat-up rates, presinter temperatures, holding times, and cool-down times may be chosen, which must be tuned relative to each other in such a way that they yield a surface porosity of the presintered green compact, which may also be referred to as blank, of between 16% and 22%.

In particular, the parameters should be tuned in such a way that they yield a surface porosity between 18% and 20%.

In particular it is intended that prior to debinding the green compact possess a porosity that is not more than 5% higher than the surface porosity after the presintering. In particular, this difference should not exceed 2%.

Consequently, the invention is also characterized by the fact that the compacted green compact that is used in the manufacture of the shaped body possesses a porosity between 16% and 27%, in particular between 18% and 22%.

If the porosity of the compacted green compact prior to debinding is always above the porosity of the presintered green compact, i.e. the blank, then the porosity may also be equal without leaving the scope of the invention.

A correlation exists between the heat-up rate, the presinter end temperature, the holding time, and the cool-down rate. For example for lower heat-up and cool-down rates one should select shorter holding times. The reverse also applies. All rates and holding times are decisively determined by the choice of presinter end temperature. Holding times shorter than 5 min are less suitable, since in particular for blanks of larger sizes a homogeneous heat penetration and presintering can not be ensured for shorter holding times. Holding times in excess of 60 min are also detrimental, since a longer dwell time favours the undesired formation of an oxidation layer.

Shaped bodies with a corresponding surface porosity possess excellent machining characteristics to allow production of in particular a dental prosthesis or part thereof. Highly precise machining can be performed with low tool wear.

After cooling the blank to room temperature, material-removing machining is performed to create the shaped body, whereby the processes of milling and grinding shall be named.

The final step performed is the one of sintering to full density.

It is in particular intended to use as metal powder a nickel-chromium-based or cobalt-chromium-based metal powder, in particular a dental alloy powder in the form of a cobalt-chromium alloy, preferably a cobalt-chromium-molybdenum alloy.

Preferred binding agents are wax- and/or cellulose-based binding agents.

In particular it is intended that for the purpose of achieving a surface porosity between 16% and 22%, in particular between 18% and 20%, the green compact be held at the presinter end temperature $T_{VS}$ for a time period $t_{VS}$ in accordance with the relation $$t/2 < t_{VS} < 2t \qquad (1).$$

t is computed using the equation:

$$t = t_0 \cdot \ln\left(\frac{c_0}{c}\right) \cdot \exp\left(\frac{T_0}{T_{VS}}\right) \qquad (2)$$

with
c=desired surface porosity fraction of the green compact after presintering,
$c_0$=surface porosity fraction of the green compact after debinding,
$t_0$=material constant in min,
$T_0$=material constant in Kelvin,
$T_{vs}$=presinter end temperature at the holding time $t_{vs}$ with 650° C.≤$T_{vs}$≤1100° C.

$c_0$, i.e. the surface porosity fraction of the green compact after debinding, can be determined by interpolation of measurement results, whereby on principle the following relation applies: $c_0-c<5\%$, in particular $c_0-c<2\%$. Preferably, one should specify as additional condition: $c<c_0$.

The material constant $t_0$ can also be determined by interpolation of measurement results. When using cobalt-chromium-based metal powder or equivalent materials one finds $t_0$=0.0125 min.

When using cobalt-chromium-based or equivalent metal powder the corresponding material constant will be $T_0$=11000 K.

It should be noted that $T_{VS}$ is to be entered in the above equation in Kelvin rather than in degree Celsius.

If the presintering in accordance with this relation is performed by holding the presinter end temperature for the duration of a holding time $t_{VS}$, then cool-down and heat-up rates should be chosen to be so short that the bulk of the presintering will take place during the holding time. In particular, during heating with a nearly constant heat-up rate $R_{HVS}$ and cooling with a nearly constant cool-down rate $R_{KVS}$, the heat-up period between 650° C. and the presinter end temperature $T_{VS}$ and the cooling period between the presinter end temperature $T_{VS}$ and 650° C. should satisfy the following relation:

$$\frac{T_{VS} - 650° C.}{R_{HVS}} + \frac{T_{VS} - 650° C.}{R_{KVS}} < 2t, \qquad (3)$$

whereby temperatures should be specified in degree Celsius. An additional condition that must be satisfied is that the presinter end temperature $T_{VS}$ and the difference between $c_0$ and c are tuned relative to each other so that negative heat-up and cool-down rates are ruled out. Moreover, the maximum presinter end temperature $T_{VS}$ should not exceed 1100° C.

Consequently, relation (3) represents a condition that must be satisfied by the specified parameters in order to be able to use a cobalt-chromium-based or equivalent metal powder to produce a presintered blank that possesses a surface porosity between 16% and 22%.

Surprisingly it has been realized that a presintered blank—irrespective of the existing surface porosity—not only can be machined with the desired accuracy, but that in addition after the final sintering an absolutely void-free veneering is possible irrespective of the residual surface porosity. The reason for this most likely is that the presinter steps and specified parameters according to the invention result in a residual surface porosity that after complete sintering does not form a connected system but exists in isolated occurrences. This does not only provide the option of a non-porous ceramic veneering, as already mentioned, but also ensures the necessary corrosion resistance. It could further be determined that the necessary dimensional accuracy can be achieved after machining and the subsequent dense-sintering, i.e. that the contraction is uniform and shape-preserving.

As a further development of the invention, it is intended that the mixture of alloy powder and binding agent be subjected to axial or isostatic pressing at a pressure p with 100 MPa≤p≤1,000 MPa, in particular with 200 MPa≤p≤600 Mpa.

It is further preferred and intended that the green compact or the debindered green compact and the presintered green compact be heated under an inert-gas or forming-gas atmosphere or in vacuum. These measures ensure that only a very thin oxide layer accumulates on the surface, which can be easily removed, e.g. by polishing, without the polishing after the complete-sintering being affected by the residual surface porosity.

The blank produced in this manner can subsequently be machined using in particular wet- or dry-working tools, whereby in particular with CAM technology the blank can be used to created any desired number of shaped bodies with corresponding dimensions, in particular of dental prostheses such as crowns or bridges, in particular by milling or grinding. Profiling also represents a viable option.

The invention is further characterized by a green compact intended for the manufacture of a dental prosthesis or part thereof, whereby the green compact is a presintered green compact made from a dental metal alloy and possesses a surface porosity of between 16% and 22%. It is particularly intended that the dental metal alloy be a nickel-chromium or cobalt-chromium alloy.

In particular it is intended that as dental alloy metal powder one use a mixture of 50% to 70% by weight of cobalt, 20% to 35% by weight of chromium, 0% to 10% of weight by molybdenum, 0% to 20% by weight of tungsten, less than 10% by weight of one or several other elements, in particular one or several elements from the group comprising manganese, silicon, nickel, beryllium, cadmium, lead, iron, aluminum, titanium, oxygen, nitrogen, and sulphur, with possible use of other elements with a weight fraction of less than 1% by weight, whereby the sum total adds up to 100%.

The invention is further characterized by the fact that one uses as dental alloy metal powder a mixture of 50% to 70% by weight of nickel, 20% to 35% by weight of chromium, 0% to 10% by weight of molybdenum, 0% to 20% by weight of tungsten, and less than 10% by weight of one or several other elements, in particular one or several elements from the group manganese, silicon, cobalt, beryllium, cadmium, lead, iron, aluminum, titanium, oxygen, nitrogen, sulphur, and possible other elements with a weight fraction of less than 1% by weight, whereby the sum total is 100% by weight.

Further details, advantages, and features are not only found in the claims and the characteristic features specified therein, but also in the following description of preferred embodiment examples.

In the manufacture of a dental prosthesis we used a metal alloy with the composition
26 to 30% by weight of Cr,
5 to 7% by weight of Mo,
in total between 0.01 and 1.5% by weight of at least one of the elements Mn, Si, Fe, C, Ni,
remainder Co (61.5% to 68.99% by weight)
whereby the sum total is 100% by weight. To produce the powder, we at first produced, melted, and atomized a metal alloy. The mean grain size was in the region between 5 μm and 50 μm. Subsequently a wax-based binding agent was added, specifically approximately 2% by weight of the metal powder. The mixture produced in this manner was subjected to axial pressing to produce green compacts with a disk-shaped geometry. The diameter was approximately 10 cm and the thickness approximately 1 cm. Different dimensions are feasible.

This was followed by debinding. For this, the green compacts were at first heated to 450° C. using any desired heat-up rate. Heat-up above 450° C. occurred slowly, whereby we chose 3 K/min as preferred heat-up rate. After reaching the temperature $T_2$, which was approximately 600° C., the green compacts were held there for a time $t_1$ of approximately 10 min. These parameters are in principle sufficient to ensure elimination of the binding agent.

A green compact that had been subjected to debinding was subsequently presintered to create a CoCrMo blank. For this purpose, the green compact—in accordance with an alternative method—was rapidly heated to a temperature in the region of approximately 800° C. (heat-up rate in the region of 90 K/min) and was held at this temperature for a time period of approximately 20 min. This was followed by cooling, which initially took place at a constant rate and then at a lower rate.

This method satisfied the relations and conditions of equations (1), (2), and (3):

$$t = t_0 \cdot \ln\left(\frac{c_0}{c}\right) \cdot \exp\left(\frac{T_0}{T_{VS}}\right)$$
$$= 0.0125 \text{ min} \cdot \ln\left(\frac{0.20}{0.19}\right) \cdot \exp\left(\frac{11000K}{1073K}\right) \approx 18 \text{ min}$$

and thus $t/2 < t_{VS} < 2t$, in this case 9 min $< t_{VS} <$ 36 min and $$\frac{T_{VS} - 650° \text{ C.}}{R_{HVS}} + \frac{T_{VS} - 650° \text{ C.}}{R_{KVS}} < 2t$$

here:

$$\frac{800° \text{ C.} - 650° \text{ C.}}{90K/\text{min}} + \frac{800° \text{ C.} - 650° \text{ C.}}{90K/\text{min}} \approx 3.3 \text{ min} < 36 \text{ min}$$

Micrographs of blanks produced in this manner showed an open surface porosity in a range between 16% and 22%, with a large number between 18% and 20%. These blanks were easy to work with, without any risk of high tool wear, which is known to have a detrimental effect on the precision of the machining.

The surface porosity allowed an uncomplicated processing using a CAM machine. For this, the blank was mounted in the CAM machine using a holding device. This was followed by material-removing machining, whereby regions of the blank were machined using a wet system and a dry system. When milling dry, the dust generated during the machining was removed by means of a class-H vacuum cleaner. The wet processes used were grinding processes. In particular when using the wet machining, no disadvantages were encountered.

The bodies machined from the blank possessed dimensions that took into account the contraction occurring during sintering to final density. After contraction we determined that the contraction took place uniformly and in a shape-preserving manner. Subsequently, the surface of the shaped body was polished or a ceramic veneer was attached in the usual manner, which could be achieved in an absolutely void-free manner, without the existing residual surface porosity causing any problems.

Even though the invention was explained using the example of dental prostheses, this shall not place any limitations on the invention.

What is claimed is:

1. A method for the manufacture of a shaped body, a dental prosthesis, or part thereof, the method comprising:
    preparing a mixture of a metal powder and a binding agent;
    compacting the mixture to form a green compact;
    heating the green compact from room temperature to a debinding start temperature $T_1$;
    debinding the green compact, wherein the green compact at first is heated to the debinding start temperature $T_1$, with 350° C.$\leq T_1 \leq$550° C., and subsequently is heated in a temperature range between $T_1$ and the debinding temperature $T_2$, with 550° C.$\leq T_2 \leq$650° C., and wherein $T_2 > T_1$, at a heat-up rate $R_1$, with 1 K/min$\leq R_1 \leq$5 K/min, to $T_2$, so that the green compact suffers no damage;
    presintering of the debindered green compact to a presinter end temperature $T_{VS}$ at a heat-up rate $R_{HVS}$;
    cooling the green compact from the presinter end temperature $T_{VS}$ at a cooling rate $R_{KVS}$, whereby at least the heat-up rate $R_{HVS}$, the presinter end temperature $T_{VS}$, and the cooling rate $R_{KVS}$ are tuned relative to each other in such a way that the presintered green compact, forming a blank, possesses a surface porosity between 16% and 22% after presintering,
    material-removing machining of the blank; and
    sintering to final density of the machined blank to form the shaped body.

2. The method of claim 1, characterized in that after being heated to the presinter end temperature $T_{VS}$, the green compact is held at the presinter end temperature $T_{VS}$ for the duration of a holding time $t_{VS}$ before it is cooled at the cooling rate $R_{KVS}$.

3. The method of claim 2, wherein the green compact is cooled at the cooling rate $R_{KVS}$ to a temperature $T_3$ where 450° C.$\leq T_3 \leq$650° C.

4. The method of claim 1, wherein the green compact is held at the debinding end temperature $T_2$ for a time period $t_2$ with 1 min$\leq t_2 \leq$20 min.

5. The method of claim 1, characterized in that the compacted green compact used is a green compact with a surface porosity between 16% and 27%.

6. The method of claim 5, wherein the surface porosity of the compacted green compact is between 18% and 22%.

7. The method of claim 1, characterized in that a nickel-chromium alloy, or a cobalt-chromium alloy is used as the metal powder, wherein, for a cobalt-chromium alloy, the following composition is used:
    Cobalt: 50% to 70% by weight
    Chromium: 20% to 35% by weight Molybdenum: 0% to 10% by weight
Tungsten: 0% to 20% by weight
Other elements: less than 10% by weight,
wherein the sum total adds up to 100% by weight,
wherein, for a nickel-chromium alloy, the following composition is used:
Nickel: 50% to 70% by weight
Chromium: 20% to 35% by weight
Molybdenum: 0% to 10% by weight
Tungsten: 0% to 20% by weight
Other elements: less than 10% by weight
with a sum total of 100% by weight.

8. The method of claim 1, characterized in that the green compact is held for the duration of a holding time $t_{VS}$ at the presinter end temperature $T_{VS}$, such that when a higher $T_{VS}$ is selected, a shorter holding time $t_{VS}$ is set.

9. The method of claim 8, wherein 650° C.≤$T_{VS}$≤1100° C.

10. The method of claim 1, characterized in that for a presinter end temperature $T_{VS}$ of 650° C.≤$T_{VS}$<750° C., the holding time $t_{VS}$ is 10 min≤$t_{VS}$≤200 min.

11. The method of claim 10, wherein 30 min≤$t_{vs}$≤100 min.

12. The method of claim 10, wherein 50 min≤$t_{vs}$≤80 min.

13. The method of claim 10, wherein 1 K/min≤$R_{HVS}$≤200 K/min and 1 K/min≤$R_{KVS}$≤200 K/min.

14. The method of claim 13, wherein 1 K/min≤$R_{HVS}$≤50 K/min.

15. The method of claim 13, wherein 1 K/min≤$R_{HVS}$≤20 K/min.

16. The method of claim 13, wherein 1 K/min≤$R_{KVS}$≤50 K/min.

17. The method of claim 13, wherein 1 K/min≤$R_{KVS}$≤20 K/min.

18. The method of claim 10, wherein 1 K/min≤$R_{KVS}$≤200 K/min.

19. The method of claim 1, characterized in that for a presinter end temperature $T_{VS}$ of 750° C.≤$T_{VS}$<850° C., the holding time $t_{VS}$ is 5 min≤$t_{VS}$≤60 min, and the heat-up rate $R_{HVS}$ and the cool-down rate $R_{KVS}$ is 5 K/min≤$R_{HVS}$≤200 K/min and 5 K/min≤$R_{KVS}$≤200 K/min.

20. The method of claim 19, wherein 10 min≤$t_{vs}$≤30 min.

21. The method of claim 19 wherein 5 K/min≤$R_{HVS}$≤20 K/min.

22. The method of claim 19, wherein 5 K/min≤$R_{KVS}$≤20 K/min.

23. The method of claim 1, characterized in that, for a presinter end temperature $T_{VS}$ with 850° C.≤$T_{VS}$<950° C., the holding time $t_{VS}$ is set to 5 min≤$t_{VS}$≤30 min and 15 K/min≤$R_{KVS}$≤200 K/min.

24. The method of claim 23, wherein 10 min≤$t_{vs}$≤20 min.

25. The method of claim 23, wherein 15 K/min≤$R_{HVS}$≤200 K/min and 15 K/min≤$R_{KVS}$≤200 K/min.

26. The method of claim 25, wherein 15 K/min≤$R_{HVS}$≤50 K/min.

27. The method of claim 25, wherein 15 K/min≤$R_{KVS}$≤50 K/min.

28. The method of claim 1, characterized in that for a presinter end temperature $T_{VS}$ with 950° C.≤$T_{VS}$≤1100° C. the holding time $t_{VS}$ is set to 5 min≤$t_{VS}$≤20 min.

29. The method of claim 28, wherein 30 K/min≤$R_{HVS}$≤200 K/min and 30 K/min≤$R_{KVS}$≤200 K/min.

30. The method of claim 29, wherein 30 K/min≤$R_{HVS}$≤100 K/min.

31. The method of claim 29, wherein 30 K/min≤$R_{KVS}$≤100 K/min.

32. The method of claim 1, characterized in that the green compact is kept at a presinter end temperature $T_{VS}$ (in K) for a time period $t_{VS}$ whereby $$t/2 < t_{VS} < 2t$$

with:

$$t = t_0 \cdot \ln\left(\frac{c_0}{c}\right) \cdot \exp\left(\frac{T_0}{T_{VS}}\right)$$

with
   c=Desired surface porosity fraction of the green compact after presintering with 16%<c<22%,
   $c_0$=surface porosity fraction of the green compact after debinding with $c_0$−c<5%,
   $t_0$=matter constant with $t_0$=0.0125 min
   $T_0$=matter constant with $T_0$=11000 K
   $T_{VS}$=presinter end temperature for a holding time $t_{vs}$ with 650° C.≤$T_{VS}$≤1100° C.

33. The method of claim 32, characterized in that the heating time with an approximately constant heat-up rate $R_{HVS}$ and the cooling time with an approximately constant cool-down rate $R_{KVS}$ are set within the range between 650° C. and the presinter end temperature $T_{VS}$, specified in degree Celsius, in a way so that they satisfy the condition:

$$\frac{T_{VS} - 650° C.}{R_{HVS}} + \frac{T_{VS} - 650° C.}{R_{KVS}} < 2t$$

whereby $$t = t_0 \cdot \ln\left(\frac{c_0}{c}\right) \cdot \exp\left(\frac{T_0}{T_{VS}}\right)$$

and $T_{VS}$ and $c_0$−c are tuned relative to each other so that negative heat-up and cool-down times are ruled out.

34. The method of claim 32, wherein $c_0$−c<2%.

35. The method of claim 32, wherein $c_0$>c.

36. The method of claim 32, wherein 18%<c<20%.

37. The method of claim 1, characterized in that the metal alloy is atomized into a powder and is mixed with a wax- and/or cellulose-based binding agent to produce a mixture.

38. The method of claim 37, wherein the green compact is produced by way of isostatic or axial pressing of the mixture consisting of the metal powder and the binding agent, at a pressure p with 100 MPa≤p≤1,000 MPa, or using a metal powder injection moulding process.

39. The method of claim 38, wherein 200 MPa≤p≤600 MPa.

40. The method of claim 37, wherein at least the debinding and presintering are carried out in the absence of oxygen.

41. The method of claim 40, wherein at least the debinding and presintering are carried out in a member selected from the group consisting of an inert gas atmosphere, a reducing atmosphere, a forming gas atmosphere, and a vacuum.

* * * * *